(12) United States Patent
Legemah et al.

(10) Patent No.: US 9,534,167 B2
(45) Date of Patent: Jan. 3, 2017

(54) FRACTURING METHOD USING POLYBORONIC COMPOUND

(71) Applicant: Baker Hughes Incorporated, Houston, TX (US)

(72) Inventors: Magnus Legemah, Richmond, TX (US); Hong Sun, Houston, TX (US); Michael Guerin, Spring, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 606 days.

(21) Appl. No.: 13/736,799

(22) Filed: Jan. 8, 2013

(65) Prior Publication Data

US 2013/0220621 A1 Aug. 29, 2013

Related U.S. Application Data

(63) Continuation-in-part of application No. 12/580,322, filed on Oct. 16, 2009, now Pat. No. 8,420,577, and a continuation-in-part of application No. 12/255,125, filed on Oct. 21, 2008, now Pat. No. 8,173,580.

(51) Int. Cl.
*C09K 8/68* (2006.01)
*E21B 43/26* (2006.01)
*C07F 5/02* (2006.01)

(52) U.S. Cl.
CPC .............. *C09K 8/685* (2013.01); *C07F 5/02* (2013.01); *C07F 5/025* (2013.01); *E21B 43/26* (2013.01)

(58) Field of Classification Search
None
See application file for complete search history.

(56) References Cited

U.S. PATENT DOCUMENTS

| | | |
|---|---|---|
| 3,284,410 A | 11/1966 | Meinhardt |
| 3,693,720 A | 9/1972 | McDougall et al. |
| 3,974,077 A | 8/1976 | Free |
| 4,328,113 A | 5/1982 | Horodysky et al. |
| 4,474,671 A | 10/1984 | Herd et al. |
| 4,619,776 A | 10/1986 | Mondshine |
| 4,635,727 A | 1/1987 | Anderson et al. |
| 5,145,590 A | 9/1992 | Dawson |
| 5,305,832 A | 4/1994 | Gupta et al. |
| 5,856,507 A | 1/1999 | Polniaszek et al. |

(Continued)

FOREIGN PATENT DOCUMENTS

| | | |
|---|---|---|
| GB | 922667 | 4/1963 |
| GB | 1545629 B2 | 5/1979 |

OTHER PUBLICATIONS

Wiskur, et al, "pKa Values and Geometries of Secondary and Tertiary Amines Complexed to Boronic Acids—Implications for Sensor Design", Organic Letters, vol. 3, No. 9, 2001, pp. 1311-1314.

(Continued)

*Primary Examiner* — John J Figueroa
(74) *Attorney, Agent, or Firm* — John Wilson Jones

(57) ABSTRACT

Polyboronic compounds useful as delayed crosslinking agents may be produced by using a polyamine as base scaffold and incorporating boron via reaction with intermediate borates which may be formed in the condensation reaction between boric acid and a diol. A di-aldehyde, such as glyoxal, may be introduced following caustic treatment of the reaction mixture of polyaminoboronate to form the polyboronic compound.

25 Claims, 5 Drawing Sheets

(56) References Cited

U.S. PATENT DOCUMENTS

| | | |
|---|---|---|
| 5,972,850 A | 10/1999 | Nimerick |
| 6,017,855 A | 1/2000 | Dawson et al. |
| 6,060,436 A | 5/2000 | Snyder et al. |
| 7,572,757 B1 | 8/2009 | Gupta et al. |
| 7,741,253 B2 | 6/2010 | Hanes, Jr. |
| 8,173,580 B2 | 5/2012 | De Benedictis et al. |
| 8,389,763 B2 | 3/2013 | Sun et al. |
| 8,420,577 B2 | 4/2013 | Sun et al. |
| 8,691,735 B2 | 4/2014 | Sun et al. |
| 2002/0061288 A1 | 5/2002 | Hubbell et al. |
| 2002/0068826 A1 | 6/2002 | Song et al. |
| 2006/0003900 A1 | 1/2006 | Hanes, Jr. |
| 2006/0089265 A1 | 4/2006 | Hanes, Jr. et al. |
| 2007/0179067 A1* | 8/2007 | Noble et al. .......... 508/188 |
| 2007/0267193 A1 | 11/2007 | Hills et al. |
| 2009/0298719 A1 | 12/2009 | Le et al. |
| 2010/0016182 A1 | 1/2010 | Gupta et al. |
| 2010/0056403 A1 | 3/2010 | Abad et al. |
| 2010/0099913 A1 | 4/2010 | Sun et al. |
| 2010/0197966 A1 | 8/2010 | Sun et al. |
| 2012/0310011 A1* | 12/2012 | Sun .......... C07F 5/025 564/9 |

OTHER PUBLICATIONS

Lei, Cuiyue, et al., Crosslinking of Guar and Guar Derivatives, SPE Annual Technical Conference and Exhibition, Sep. 26-29, 2004, Houston, TX.

Lei, Cuiyue, et al., Fracturing-Fluid Crosslinking at Low Polymer Concentration, SPE Annual Technical Conference and Exhibition, Oct. 9-12, 2005, Dallas, TX.

C. Lie et al., "Fracturing-Fluid Crosslinking at Low Polymer Concentration", SPE 96937, pp. 1-6, Oct. 9-12, 2005.

B. D. Vineyard et al, "A Study of the Reaction of Boric Acid with Amines: Hydroxyboroxin-Amine Salts", Inorganic chemistry, 1964, pp. 1144.

Arag, F. et al., "Complexes of Boric Acid with Amines", Z. anorg. allg. Chem., 357: 107-108: doi 10.1002/zzaac.19683570113 (Abstract), pp. 1-3, 1968.

* cited by examiner

FRACTURING METHOD USING POLYBORONIC COMPOUND

CROSS REFERENCE TO RELATED APPLICATIONS

The present application is a continuation-in-part patent application of U.S. patent application Ser. No. 12/580,322, filed Oct. 16, 2009, which is a continuation-in-part application of U.S. patent application Ser. No. 12/255,125, filed Oct. 21, 2008, now U.S. Pat. No. 8,173,580.

BACKGROUND OF THE INVENTION

Field of the Invention

The present invention relates to polyboronic compounds, compositions containing such compounds and methods of making and using the same.

Description of the Related Art

Hydraulic fracturing techniques are widely used to enhance oil and gas production from subterranean formations. During hydraulic fracturing, a fluid is injected into a well bore under high pressure. Once the natural reservoir fracture gradient is exceeded, the fracturing fluid initiates a fracture in the formation that generally continues to grow during pumping. The treatment design generally requires the fluid to reach a maximum viscosity as it enters the fracture that affects the fracture length and width. The viscosity of most fracturing fluids is generated from water-soluble polysaccharides, such as galactomannans or cellulose derivatives.

The gelled fluid can be accompanied by a propping agent (i.e., proppant) that results in placement of the proppant within the fracture that has been produced. The proppant remains in the produced fracture to prevent the complete closure of the fracture and to form a conductive channel extending from the well bore into the formation being treated once the fracturing fluid is recovered.

Guar based fracturing fluids are the most commonly used fluids in reservoir stimulation. Guar is composed of polymannose backbone with galactose branching with an approximate ratio of 2:1. The solubility of guar gum is greatly enhanced by the galactose branching compared to other polysaccharides.

Hydrated guar or its derivative (linear gel) at ambient temperature does not possess the required viscosity for proppant transport. Thus, crosslinkers, such as boron, zirconium, titanium compounds, are used to significantly improve viscosity of the fluid system. Hydrated guar gum is mostly crosslinked with borates while derivatized guar gums such as, carboxymethyl guar (CMG), hydroxypropyl guar (HPG) and carboxymethyl hydroxypropyl guar (CMHPG), are mostly crosslinked with transition metals. Borate crosslinked fluids are typically preferred due to their reversibility to mechanical shearing and favorable environmental properties.

Pumping fluids with high viscosity requires tremendous amount of horsepower due to high pipe friction, so delayed crosslinkers are desired. Further, while boron and zirconium crosslinking agents are effective for many types of fracturing fluids containing hydratable polymers, a certain amount of the polymer is needed to achieve the viscosity necessary to fractionate the formation. It is desirable to use as little polymer as possible in a fracturing fluid so that the overall cost of the fracturing job is lower. With reduced polymer loading, less polymer residue remains in the fracture and the sand pack after breaking. Formation damage is therefore minimized.

In view of the foregoing, a need exists for a crosslinking agent that would effectively increase the viscosity of the polymer, which also reduces the polymer loading as much as possible in fracturing fluids. In addition, a need exists for agents which are capable of exhibiting delayed crosslinking activity. A need also exists for compounds, such as polyboronic compounds, that can be prepared and have more than one B—N bond that helps with functions, such as crosslinking. Additionally, it would be advantageous if such crosslinking system is compatible with existing fracturing systems.

SUMMARY OF THE INVENTION

In view of the foregoing, crosslinked fracturing fluids and methods of fracturing subterranean formations are provided as embodiments of the present invention. The compositions and methods described herein are effective and allow for lower polymer loadings in fracturing jobs.

As an embodiment of the present invention, a fracturing fluid composition is provided. In this embodiment, the fracturing fluid includes a hydratable polymer capable of gelling in the presence of a crosslinking agent comprising a polyboronic compound.

Besides the compositional embodiments, methods of fracturing subterranean formations are also provided as embodiments of the present invention. For example, as another embodiment of the present invention, a method of fracturing a subterranean formation is provided. In this embodiment, water and a hydratable polymer capable of gelling are blended together and allowed to hydrate to form a hydrated polymer solution. Once the hydrated polymer solution is formed, a crosslinking agent comprising a polyboronic compound is added to the hydrated polymer solution to produce a crosslinked fracturing fluid. The crosslinked fracturing fluid is then injected into the subterranean formation to fracture the formation.

As another example, a method of fracturing a subterranean formation is provided as an embodiment of the present invention. In this embodiment, a fracturing fluid comprising a hydratable polymer is crosslinked by contacting the fracturing fluid with a polyboronic compound to produce a crosslinked fracturing fluid. The crosslinked fracturing fluid of the present invention has a higher viscosity when compared with the fracturing fluid being crosslinked with a conventional borate-crosslinked fluid with the same polymer loading.

The increased viscosity of the crosslinked fracturing fluid of the present invention allows for a less amount of polymer to be used to achieve comparable results as prior art crosslinked fracturing fluids having higher polymer loadings. The resulting fracturing fluid of the present invention has a lower $C_{cc}$ (critical crosslinking concentration) than the same polymer being crosslinked with conventional boric acid crosslinking agent.

In addition to the crosslinking agent, as an embodiment of the present invention, polyboronic compounds and methods of making them are provided as embodiments of the present invention. The polyboronic compounds and methods of making them described herein can be used as crosslinking agents in compositions and methods described herein. It is believed that they can also be used in other applications, as well.

Figure 1:
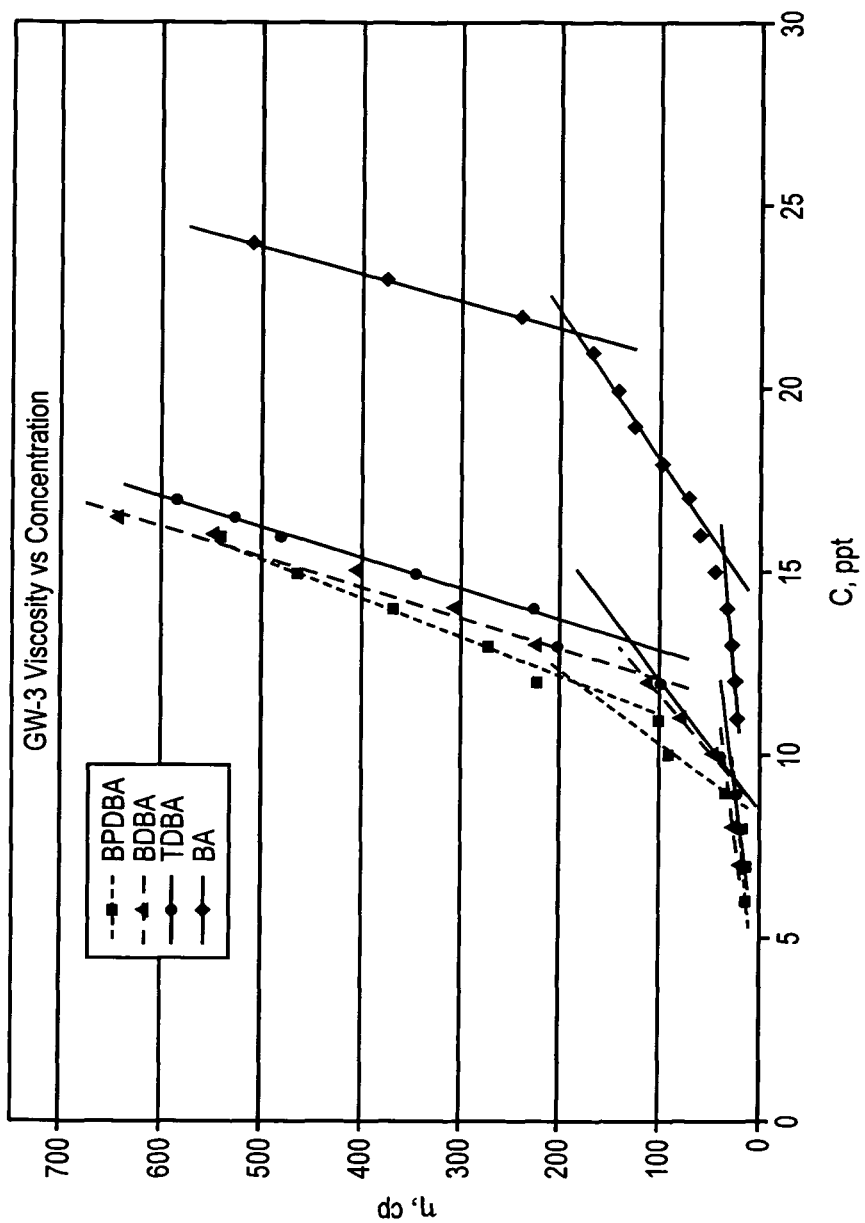
FIG. 1 is a chart showing the viscosity (cP) of GW-3 guar at various concentrations (ppt) using various crosslinking agents in accordance with embodiments of the present invention.

While the invention is susceptible to various modifications and alternative forms, specific embodiments have been shown by way of example in the drawings and will be described in detail herein. However, it should be understood that the invention is not intended to be limited to the particular forms disclosed. Rather, the intention is to cover all modifications, equivalents and alternatives falling within the spirit and scope of the invention as defined by the appended claims.

DESCRIPTION OF ILLUSTRATIVE EMBODIMENTS

Illustrative embodiments of the invention are described below as they might be employed in the operation and in the treatment of oilfield applications. In the interest of clarity, not all features of an actual implementation are described in this specification. It will of course be appreciated that in the development of any such actual embodiment, numerous implementation-specific decisions must be made to achieve the developers' specific goals, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments of the invention will become apparent from consideration of the following description.

As an embodiment of the present invention, a crosslinked fracturing fluid composition is provided. In this embodiment, the fracturing fluid includes a hydratable polymer capable of gelling in the presence of a crosslinking agent comprising a polyboronic compound. Typical hydratable polymers include, not limited to, polysaccharide, guar gum, guar gum derivatives, locust bean gum, karaya gum, carboxymethyl cellulose, carboxymethylhydroxyethyl cellulose, hydroxyethyl cellulose, or combinations thereof. Various types of polyboronic compounds can be used in embodiments of the present invention, as described herein. Conventional boron crosslinking agents used in hydraulic fracturing fluids are generally composed of borate salts or esters. The polyboronic compounds of the present invention are more effective when compared to the conventional boron crosslinking agents, which enables users to lower the polymer loading for fracturing jobs.

Besides the compositional embodiments, methods of fracturing subterranean formations are also provided as embodiments of the present invention. For example, as another embodiment of the present invention, a method of fracturing a subterranean formation is provided. In this embodiment, water and a hydratable polymer capable of gelling in the presence of a crosslinking agent are blended together and allowed to hydrate to form a hydrated polymer solution. Once the hydrated polymer solution is formed, a crosslinking agent comprising a polyboronic compound is added to the hydrated polymer solution to produce a crosslinked fracturing fluid. The crosslinked fracturing fluid is then injected into the subterranean formation to fracture the formation.

As another example, a method of fracturing a subterranean formation is provided as an embodiment of the present invention. In this embodiment, a fracturing fluid comprising a hydratable polymer is crosslinked by contacting the fracturing fluid with a polyboronic compound to produce a crosslinked fracturing fluid. The crosslinked fracturing fluid of the present invention has a higher viscosity when compared with the fracturing fluid being crosslinked with conventional boric acid crosslinking agents. The crosslinked fracturing fluid is then injected into the subterranean formation to fracture the formation.

The amounts of the components within the fracturing fluid can be varied in various embodiments of the present invention. For example, the polyboronic compound can be present in a range of about 0.02 vol. % to about 0.5 vol. % of the fracturing fluid composition; alternatively, in a range of about 0.10 vol. % to about 0.25 vol. %. In an aspect, the polyboronic compounds can be present in a range that is effective for achieving the desired viscosity of the resulting fracturing fluid, as will be apparent to those of skill in the art.

The methods and compositions described herein can be used with various types of fracturing fluid systems. The hydratable polymer can be varied depending upon the needs of a particular fracturing job. For example, the hydratable polymer can be guar gum, guar gum derivatives, locust bean gum, karaya gum, carboxymethyl cellulose, carboxymethylhydroxyethyl cellulose, hydroxyethyl cellulose, or combinations thereof. Other suitable hydratable polymers that are compatible with the methods and compositions described herein can be used and are to be considered within the scope of the present invention.

The methods and the compositions described herein are very efficient and have a lower polymer loading when compared with the same polymer system being crosslinked using conventional crosslinking agents, such as boric acid. The methods and compositions described herein can have a higher viscosity when compared with the same amount of polymer that has been crosslinked with conventional crosslinking agents, such as boric acid. In an aspect, the fracturing fluid composition of the present invention has a $C_{cc}$ of less than about 12 ppt. In another aspect, the fracturing fluid composition of the present invention has a $C_{cc}$ less than about 15.5 ppt.

In an aspect, various compounds can be used as the polyboronic compound used in embodiments of the present invention.

Suitable polyboronic compounds can include 2,5-thiophenediboronic acid (TDBA), 1,4-benzenediboronic acid (BDBA), 4,4'-biphenyldiboronic acid (BPDBA), or combinations thereof. In an aspect, the polyboronic compounds can include compounds having the following structures:

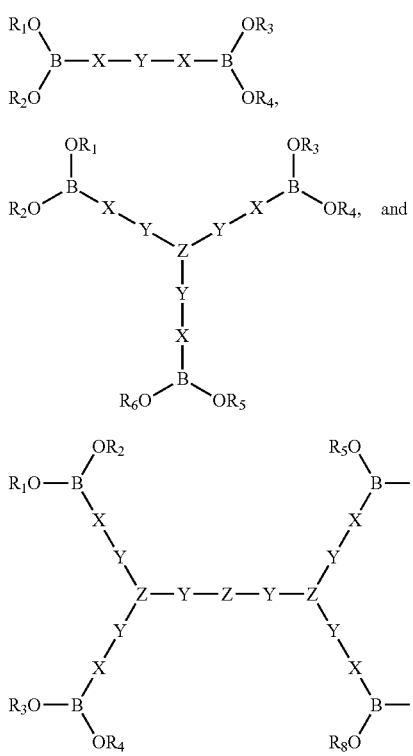

or combinations thereof, wherein, $R_1$-$R_8$ can be hydrogen, alkyl group, alkenyl group, alkynyl group, aryl group, or combinations thereof. $R_1$-$R_8$ can be, but is not required to be, identical and they can also be from the same fragment to form ring structures (such as, $R_1$, $R_2$=—$CH_2CH_2$—, —$C(CH_3)_2C(CH_3)_2$—, etc); X can be carbon, nitrogen, silicon, or combinations thereof. In an aspect, a compound with X being nitrogen to incorporate multiple boron atoms into the structure by the chemical bonding between N and B atoms is acceptable. Y can be a spacer, which can be straight chain of —($CH_2$)—, straight chain with pendant(s), straight chain with branching, aromatic ring(s) directly connected, aromatic ring(s) indirectly connected, fused aromatic rings, heterocyclic ring(s) directly connected, heterocyclic ring(s) indirectly connected, fused heterocyclic rings, aliphatic ring(s) directly connected, aliphatic ring(s) indirectly connected, fused aliphatic rings, or combinations thereof. For example, Y can be phenylene, biphenylene, triphenylene, fluorene, fluorenone, naphthalene, methylene bisphenylene, stilbene, or combinations thereof. In an aspect, X can also be part of Y when Y has ring structure(s). Z can be carbon, silicon, oxygen, nitrogen, alkyl group, alkenyl group, alkynyl group, aromatic ring(s), aliphatic ring(s), heterocyclic ring(s), or combinations thereof. Z can also be a metal atom, such as, Al, Zr, Ti, Zn, or the like connected to other parts of the structure via chelation and/or other chemical interactions. Z can also be a fragment of Y. The general structure of suitable polyboronic compounds can be further extended to dendrimeric "poly" boronic compounds. Other suitable types of polyboronic compounds will be understood by those of skill in the art and are to be considered within the scope of the present invention.

Other suitable polyboronic compounds include those of the formula:

wherein:

s is 1 to 6 and is preferably greater than 2;

each $R_9$ is independently selected from the group consisting of —W or —($CH_2$)$_r$—NH—W;

each r is independently selected from 2 to 6;

W is a substituent of the formula:

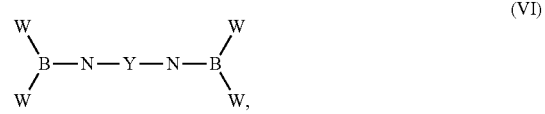

v is either 2 or 3, provided v cannot be both 2 and 3 in the same compound;

each $R_{10}$ is independently selected from either —H or $R_{12}$ and each $R_{11}$ is independently selected from either —H or —OH, provided that $R_{10}$ and $R_{11}$ in at least one W substituent group is $R_{12}$ and —OH, respectively;

each $R_{12}$ is independently selected from the group consisting of a linear or branched $C_1$-$C_6$ alkyl or alkenyl group, optionally substituted with —X or —$OR_{13}$;

X is —Cl or —Br; and $R_{13}$ is a $C_1$-$C_6$ alkyl group.

Such polyboronic compounds are particularly effective as delayed crosslinkers. As such, the polyboronic compounds improve the control of fluid viscosity buildup.

In a preferred embodiment, at least two of the W substituent groups on the polyboronic compound are of formula (V). The number of W substituent groups on the polyboronic compound of formula (IV) is preferably from 1 to 4.

In one preferred embodiment, the polyboronic compound is formula (IV), wherein $R_9$ is —($CH_2$)$_r$—NH—W, each r is 2, s is 3 and v is 2.

In another preferred embodiment, the polyboronic compound may be of formulae:

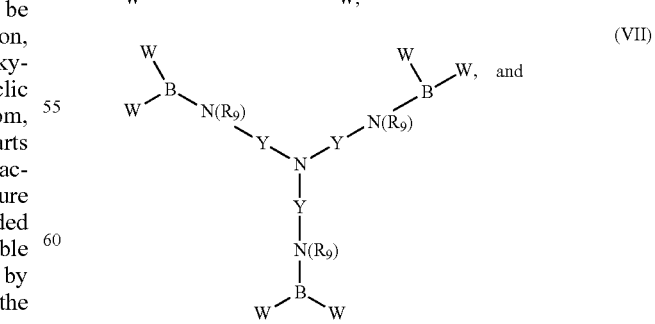

-continued

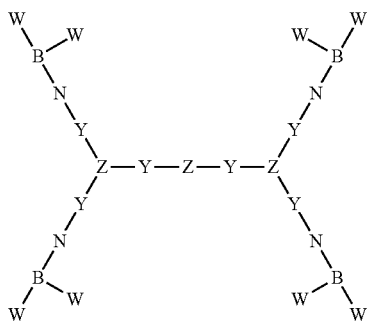

(VIII)

wherein Y is —(CH$_2$)$_r$ and Z is —CH.

In another preferred embodiment, the polyboronic compound is of formula (IX):

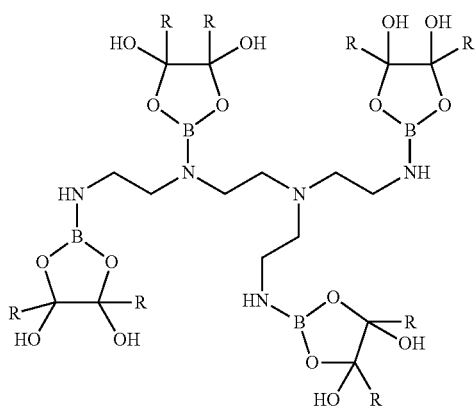

(IX)

The polyboronic compounds belong to a different type of chemistry from conventional boric acid, its ester derivatives and polyboric acids and their salts. In the chemistry nature of these boric acids or their derivatives, boron atoms are not connected to any atom other than oxygen, which leads to hydrolyzation in aqueous solution and release of boric acid. When used as crosslinking agents, the actual crosslinking species is boric acid after hydrolysis of borate esters or polyborates. When boron atom is connected to at least one atom other than the oxygen atoms, especially carbon or nitrogen, the corresponding compounds are called boronic acids (or boronic esters) and they are different compounds and possess different chemical properties. When they contact water or base, even at elevated temperatures, the B—C (or B—N, B—Si, etc.) bond will not hydrolyze, and therefore the active crosslinking species is not boric acid, but polyboronic compounds instead. When these diboronic or polyboronic compounds are used as crosslinking agents, they will provide two or more boron atom sites, each is capable of being chelated with the two cis-hydroxyls in the backbone of the hydratable polymers. Therefore, a triboronic compound can crosslink three polysaccharide chains via three boron atoms within one crosslinking agent molecule. In other words, the polyboronic species are the crosslinking agents, not boric acid hydrolyzed from corresponding esters, as shown in prior art, as delayed boric acid crosslinking agents. In an aspect, when N is attached to B, to form stable (OR)$_2$BNHRHNB(OR)$_2$ structure is particularly preferred.

As crosslinkers, the polyboronic compounds increase viscosity as well as improve fluid loss control and proppant transportability of the hydratable polymer within the fluid. They further exhibit the ability to re-heal after shearing. They further are more efficient than conventional crosslinkers since they are capable of crosslinking fluids with reduced polymer loading. Thus, the polyboronic compounds provide favorable environmental properties since their use reduces formation and proppant pack damage imposed by polymer residues. Further, since reduced polymer loadings may be used with the crosslinkers, overall cost of fluids is lowered.

Besides the polymer and crosslinking agents described herein, various additives can be useful in the present invention. Additives used in the oil and gas industry and known in the art, including but not limited to, corrosion inhibitors, non-emulsifiers, iron control agents, delay additives, silt suspenders, flowback additives, pH adjusting agents, clay stabilizer, surfactants, and gel breakers, can also be used in embodiments of the present invention. Proppants including, but not limited to, frac sand, resin coated sand, quartz sand grains, ceramic proppant, tempered glass beads, rounded walnut shell fragments, aluminum pellets, and nylon pellets at desired size can also be used. Proppant is typically used in concentrations that range from about 1 pound per gallon of the fracturing fluid composition to about 8 pounds per gallon of the fracturing fluid composition. Other suitable additives useful in the present invention will be apparent to those of skill in the art and are to be considered within the scope of the present invention.

The fracturing fluid of the present invention can be used by pumping the fluid into a well bore penetrating the subterranean formation to be fractured. The fracturing fluid is injected at a rate sufficient to fracture the formation and to place proppant into the fracture.

$C^*$, $C^{**}$, and $C_{cc}$ are often used as the leading indices for polymers to be crosslinked. $C^*$, $C^{**}$ and $C_{cc}$ depend on the type of polymer being used, as well as, possibly the type of crosslinking agent used. Polymer solutions have a critical overlap concentration ($C^*$) below which no intermolecular crosslinking leading to increased viscosity can occur. $C^{**}$ is effective entanglement concentration. As used herein, the term "$C_{cc}$" is used to describe the critical crosslinking concentration for polymer chains, as will be understood by those of skill in the art. The term "$C_{cc}$" is generally considered to be minimum polymer concentration where the fluid is able to be crosslinked. It was proposed by others that $C_{cc}$ is largely independent on the type of crosslinking agent used. As a result of the findings related to the present invention, it was discovered that the conventional theory is not necessarily true. The examples described herein show that the type of crosslinking agent used can affect $C_{cc}$, which is contrary to what was previously believed. The structures of the crosslinking agents of the present invention lowered the $C_{cc}$ of guar polymer so significantly that the polymer solutions can be effectively crosslinked at concentrations much lower than widely accepted $C_{cc}$ values. Increased crosslinker size or length can lead to crosslinking of polymer solutions well below $C^*$. This translates to reduced polymer loading without a compromise in viscosity or rheology of the fracturing fluid.

An advantage of the present invention is that lower loadings of polymer can be used to obtain equivalent fracturing fluid performance at reduced overall treatment costs. The polyboronic crosslinkers described herein exhibit greater efficiency because they are capable of crosslinking fluids with reduced polymer loading. Reduced polymer loadings result in less damage to the surrounding subterranean formation after the fracturing treatment. For instance, guar based polymers have been attributed to causing damage to the fracture sand pack and reducing the effective fracture width. The present invention permits substantial reduction in the amount of polymer injected into the formation while maintaining optimal fluid properties for creating the fracture. It is of great interest to reduce formation and proppant pack damage imposed by polymer residues after breaking of the fluid. In addition, the efficiency of crosslinker can help reduce the overall cost of the fluids, especially when the industry is challenged with extreme pricing and supply fluctuations with guar.

In addition to the crosslinking agent and related compositions and methods, polyboronic compounds and methods of making them are also provided as embodiments of the present invention. The polyboronic compounds and methods of making them described herein can be used as crosslinking agents in the compositions and methods described herein. It is believed that they can also be used in other applications, as well.

In an embodiment, a method of making a polyboronic compound is provided. In this embodiment, a polymeric amine is contacted with a trialkylborate in the presence of a solvent to produce the polyboronic compound having more than one B—N bond. Excess trialkylborate can be used. Alternatively, an insufficient amount of trialkylborate can be used.

In an aspect, the polyboronic compound can have the following structures:

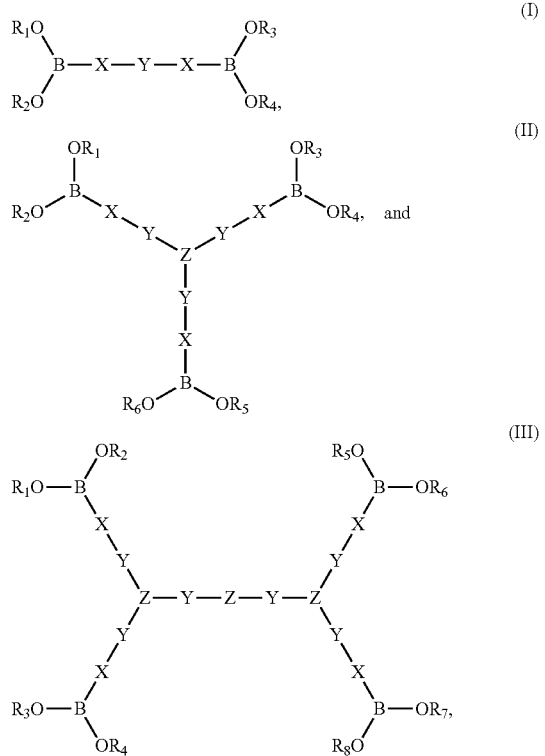

or combinations thereof, wherein $R_1$-$R_8$ is hydrogen, alkyl group, alkenyl group, alkynyl group, aryl group, or combinations thereof; X is nitrogen; Y is a straight chain of —($CH_2$)—, a straight chain with pendant(s), a straight chain with branching, aromatic ring(s) directly connected, aromatic ring(s) indirectly connected, fused aromatic rings, heterocyclic ring(s) directly connected, heterocyclic ring(s) indirectly connected, fused heterocyclic rings, aliphatic ring(s) directly connected, aliphatic ring(s) indirectly connected, fused aliphatic rings, or combinations thereof; and Z is carbon, silicon, oxygen, nitrogen, alkyl group, alkenyl group, alkynyl group, aromatic ring(s), aliphatic ring(s), heterocyclic ring(s), a metal atom, or combinations thereof.

As with other embodiments of the present invention, various types of polymeric amines can be used to produce the polyboronic compounds of the present invention. In an aspect, the polymeric amine can include ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene pentamine, ethylene tripropylene pentamine, diethylene dipropylene pentamine, triethylene propylene pentamine, polyethylenimine (e.g, Epomin® from Nippon Shokubai, Lupasol™ from BASF, Lupamine™ from BASF, etc.), poly(ethyleneoxy)amines, poly(propyleneoxy)amines (i.e., Jeffamine® T-403 from Huntsman Corporation, Polyetheramine T-5000 from BASF, etc.) or combinations thereof. Other suitable types of polymeric amines that can be used in the present invention will be apparent to those of skill in the art and are to be considered within the scope of the present invention.

Besides varying the types of polymeric amines that can be used in the present invention, the types of trialkylborates suitable in the present invention can also be varied. For example, in an aspect, the trialkylborate can include trimethylborate, triethylborate, tripropylborate, triisopropyl borate, tributyl borate, tri(tert-butyl)borate, or combinations thereof. Other suitable types of trialkylborates that can be used in the present invention will be apparent to those of skill in the art and are to be considered within the scope of the present invention.

Similarly to the polymeric amines and the trialkylborates, the types of solvents that can be used in the present invention can also be varied. For example, in an aspect, the solvent can include methanol, ethanol, propanol, 2-propanol, butanol, 2-butanol, tert-butanol, or combinations thereof. Other suitable types of solvents that can be used in the present invention will be apparent to those of skill in the art and are to be considered within the scope of the present invention.

The polyboronic compounds of the present invention have more than one B—N in the structure. The number of B—N bonds can be varied depending upon the type of polymeric amine or trialkylborate selected to produce the polyboronic compound. In an aspect, the polyboronic compound can include at least two B—N bonds. In another aspect, the polyboronic compound can include as many B—N bonds as there are N atoms in the polymeric amine.

As another embodiment of the present invention, another method of making a polyboronic compound is provided. In this embodiment, a polymeric amine is contacted with a trialkylborate in the presence of a solvent to produce the polyboronic compound. The polymeric amine comprises ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, polyethylenimine, poly(ethyleneoxy)amines, poly(propyleneoxy)amines or combinations thereof; and the polyboronic compound comprises

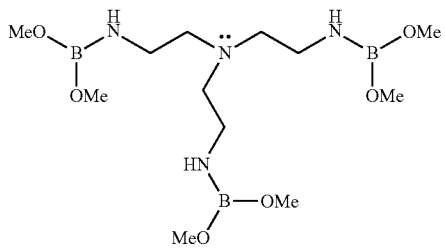

and its other ester analogs, such as ethyl boronate, etc. As with other embodiments of the present invention, excess trialkylborate can be used during the step of contacting the polymeric amine with the trialkylborate. Alternatively, an insufficient amount of trialkylborate can be used.

As yet another embodiment of the present invention, a polyboronic compound having more than one B—N bond that provides more than one borate reaction (crosslinking) site is provided. In an aspect, the polyboronic compound comprising:

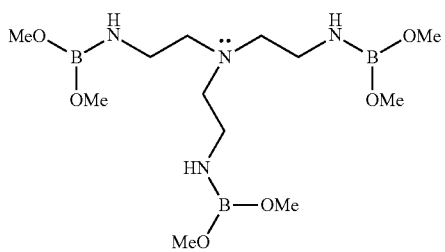

and its other ester analogs, such as ethyl boronate, etc.

In embodiments of the present invention, the polyboronic compound can include

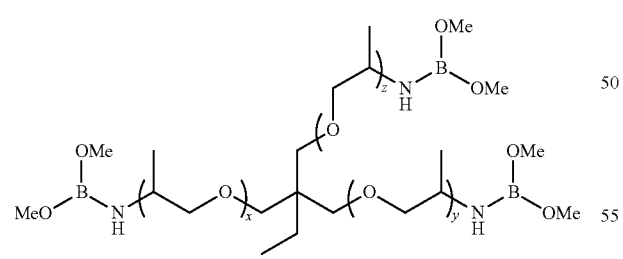

wherein the sum of x, y and z is 5 or 6. Besides this compound, its other ester analogs can also be included, such as ethyl boronate, as will be apparent to those of skill in the art and are to be considered within the scope of the present invention.

In another aspect, the polyboronic compound of formula (IV):

W—NH—(CH$_2$)$_r$-[N(R$_9$)—(CH$_2$)$_r$]$_s$—NH—W    (IV)

may be prepared by first reacting a cyclic borate ester with a polymeric amine at a temperature between from about from about 100° C. to about 180° C. Typically, the molar ratio of cyclic borate ester to polymeric amine is between from about 8:1 to about 4:1. Preferred polymeric amines include ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, or combinations thereof.

The cyclic borate ester may be of the formula (XIII):

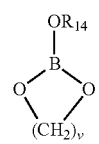 (XIII)

wherein R$_{14}$ is the alkyl chain of the alcohol solvent and wherein v is 2 or 3. Preferred solvents include ethanol, propanol, 2-propanol, butanol, 2-butanol and t-butanol and combinations thereof.

The cyclic borate ester may be prepared by reacting boric acid with a C$_2$ to C$_6$ diol, such as a 1,2-diol or 1,3-diol. Suitable diols include ethylene glycol, propylene glycol, 1,3-propanediol, 1,4-butylene diol, 1,2-butylene diol, 1,2-hexane diol as well as glycerol. The condensation reaction between boric acid and diol renders unnecessary the use of trialkylborates which are flammable. Typically, the molar ratio of boric acid and diol is from about 1:1 to about 1:8. The reaction is conducted at a temperature between from about 100 to about 180° C.

The incorporation of the cyclic borate ester into the polyamine scaffold renders a diol borate condensation product having multiple boron sites. The diol borate condensation product may be of the formula (XIV):

U—NH—(CH$_2$)$_r$-[N(R$_9$)—(CH$_2$)$_r$]$_s$—NH—U    (XIV)

wherein:
s is 1 to 6 and is preferably greater than 2;
each R$_9$ is independently selected from the group consisting of —U or —(CH$_2$), —NH—U;
each r is independently selected from 2 to 6;
U is a substituent of the formula:

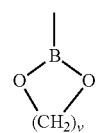 (XV)

v is either 2 or 3, provided v cannot be both 2 and 3 in the same compound.

The diol borate is then treated with caustic. Suitable as caustic is NaOH, KOH or an alkaline material or combinations thereof. The amount of caustic (expressed as 50% active caustic) introduced to the diol borate typically ranges from about 10% (based on the weight of the diol borate) to about four times. The resulting product is a polyaminoboronate (PAB) wherein the ring of at least one of the U substituents has been opened.

Following the addition of caustic, the resulting polyaminoboronate may be reacted with a di-aldehyde (preferably 1,2-dialdehydes and 3,4-dialdehydes), keto-alehydes, and di-ketones, especially those containing from 1 to about 4 carbon atoms, including glyoxal, propane dialdehyde, 2-keto propanal, 1,4-butanedial, 2-keto butanal, 2,3-butadione, etc. to render the delayed crosslinker having cyclic borate groups, represented by formula (IV). The reaction occurs typically at room temperature. Compared to polyaminoboronates (PAB) which have multiple non-cyclic aminoborate groups with non-delaying characteristics, delayed polyaminoboronates (DPAB) contain derivatized cyclic borate structures with greater delaying characteristics.

The addition of caustic prior to the addition of di-aldehyde or di-ketone ensures delay crosslinking as ring opening of the ethylene glycol borates is believed to be enhanced by the presence of caustic. Upon opening of the ring, an addition product is formed with the dialdehyde, diketone or keto-aldehyde wherein the polyborate compound containing one or more of W groups is formed.

In an embodiment, a crosslinking fluid may contain the diol borate condensate admixed with caustic. The fluid may further contain a polyol. The presence of polyol has been seen to improve the rheological properties of a fracturing fluid, as well as thermal stability performance by subjecting the polyaminoboronate to a polyol in caustic prior to reacting the polyaminoboronate with the di-aldehyde or di-ketone. Suitable polyols may include pentaerythritol, dipentaerythritol and sorbitol. The weight ratio of polyol to diol borate condensate is typically between from about 1:100 to about 20:100.

The crosslinking delay time of the polyboronic crosslinker may be adjusted by varying the amount of di-aldehyde, keto-aldehyde or di-ketone added to the caustic solution. The amount of di-aldehyde or di-ketone introduced to the polyaminoboronate is dependent on the number of cyclic borates (of formula (XV)) to be converted to derivatized borates, W. For instance, for every two cyclic borates to be converted to derivatized borates, W, an equivalent molar amount of dialdehyde or di-ketone to polyaminoboronate (PAB) should be used. A molar excess of dialdehyde or di-ketone may be used to ensure that all of the cyclic borates of formula (XV) have been converted to derivatized borates, W. Typically, the amount of di-aldehyde, keto-aldehyde or di-ketone is between from about 4 to about 15% in excess of that amount needed to convert the cyclic borates on the PAB to the derivatized borates, W, without compromising performance of the polyboronic crosslinker in the crosslinked fluid.

EXAMPLES

The following examples are included to demonstrate the use of compositions in accordance with embodiments of the present invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the scope of the invention.

Example 1

Example 1 was used to determine $C_{cc}$ and to test the effectiveness of the crosslinking agents made in accordance with embodiments of the present invention. 25 ppt (0.3%) solution of guar gum (GW-3, which is commercially available from Baker Hughes Incorporated) was prepared by hydrating GW-3 powder. After at least 30 minutes, the solution was systematically diluted to obtain 6, 7, 8, 9, 10, 11, 12, 13, 14, 15, 16, 17, 18, 19, 20, 21, 22, 23, 24 ppt solutions. Other additives (such as buffer, clay stabilizer, and bactericide) were added to the GW-3 guar solution. The crosslinking agents made in accordance with embodiments of the present invention were then added by mixing. The polymer/crosslinking agent ratio was kept constant. The viscosity of the crosslinked gel was measured on Fann 35 instrument at room temperature. The polymer/crosslinking agent ratios were as follows:

| TDBA/GW-3 = 0.079 | BDBA/GW-3 = 0.039 | BPDBA/GW-3 = 0.056 | BA/GW-3 = 0.022 |
|---|---|---|---|
| TDBA/GW-45 = 1.10 | BDBA/GW-45 = 1.13 | | BA/GW-45 = 0.2233 |

Figure 2:
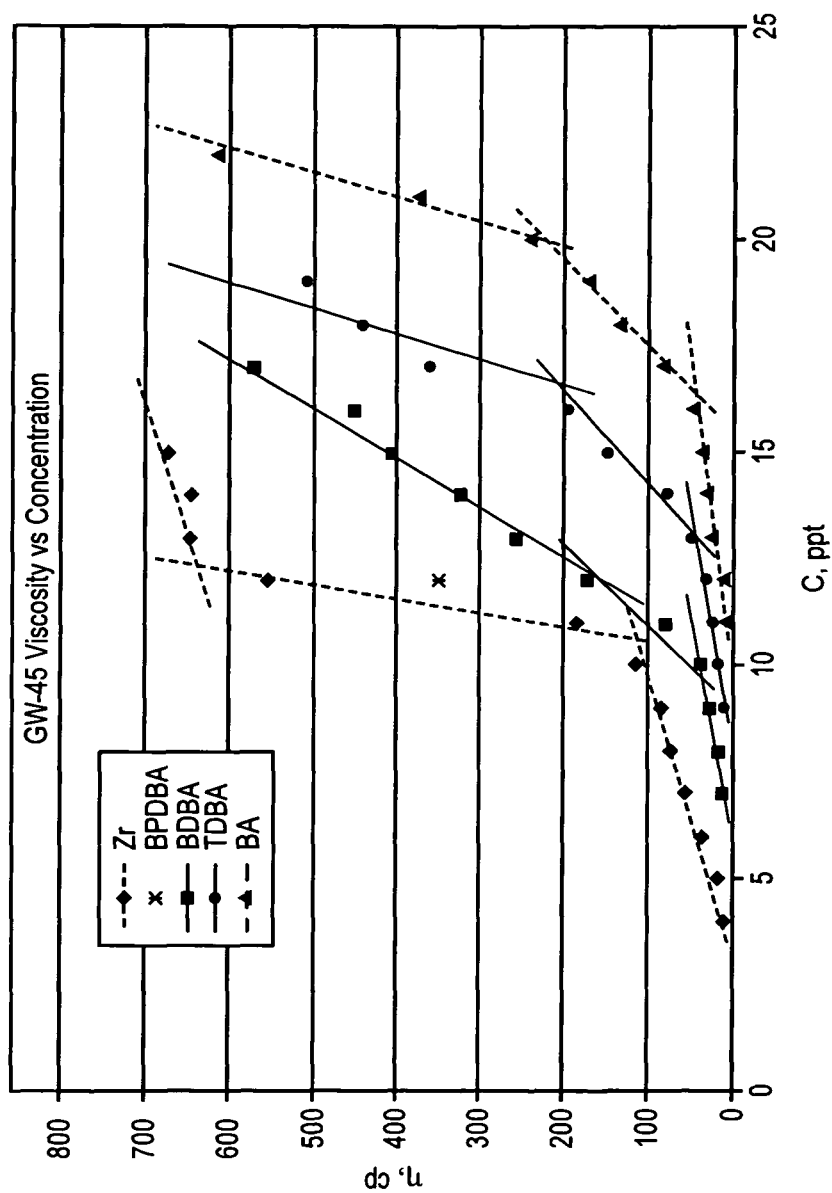
FIG. 2 is a chart showing the viscosity (cP) of GW-45 guar derivative at various concentrations (ppt) using various crosslinking agents in accordance with embodiments of the present invention.

The ratios were kept constant within each crosslinking agent to obtain systematic readings. The viscosity was plotted against the concentration to observe changes in viscosity versus concentration change, as shown in FIGS. 1 and 2. As concentration increases, a change in slope occurs. The interception of the slopes of the two regions defines $C_{cc}$.

Example 2

The $C_{cc}$ values were calculated for two different types of guar fracturing fluids, GW-3 and GW-45, that were crosslinked with four different types of crosslinking agents. GW-3 and GW-45 are guar based polymers commercially available from Baker Hughes Incorporated. As can be seen in Table 1, a lower $C_{cc}$ was obtained using the various polyboronic compounds (i.e., TDBA, BDBA, and BPDBA) when compared to the same guar polymers being crosslinked with conventional boric acid (BA). The results of this example show that the type of crosslinking agent can greatly affect the $C_{cc}$, which is contrary to what is conventionally accepted in the industry.

TABLE 1

| | $C_{cc}$, ppt | | | |
|---|---|---|---|---|
| Polymer | BA | TDBA | BDBA | BPDBA |
| GW-3 | 15 | 9 | 8.5 | 8 |
| GW-45 | 15.5 | 12 | 8.5 | |

Example 3

In this example, the viscoelastic properties (n') and viscosities (cP) of two crosslinked guar polymer systems were compared. 15 ppt of GW-3 was crosslinked with 0.27 mmol BPDBA at 150° F. and compared with a typical crosslinked system that was prepared by crosslinking 20 ppt of GW-3 with CXB-10, which is commercially available from Baker Hughes Incorporated. As shown in Table 2, the results clearly demonstrate that these polyboronic compounds used in embodiments of the present invention can effectively lower polymer loading for fracturing stimulation. The reduction of the polymer loading is related to the size of the group separating the two boronic acids.

TABLE 2

| | 15 ppt GW-3, 0.27 mmol BPDBA | | | | 20 ppt GW-3, 1 gpt CXB-10 | | |
|---|---|---|---|---|---|---|---|
| | | Viscosity (cP) at | | | | Viscosity (cP) at | |
| Time, min | n' | 40 sec$^{-1}$ | 100 sec$^{-1}$ | 170 sec$^{-1}$ | n' | 40 sec$^{-1}$ | 100 sec$^{-1}$ | 511 sec$^{-1}$ |
| 2.1 | 0.671 | 481 | 356 | 299 | 0.389 | 1855 | 1060 | 391 |
| 32.1 | 0348 | 582 | 320 | 227 | 0.533 | 349 | 228 | 106 |
| 62.1 | 0.358 | 665 | 369 | 263 | 0.871 | 343 | 305 | 247 |
| 92.1 | 0.276 | 694 | 358 | 244 | 0.753 | 317 | 253 | 169 |
| 122.1 | 0.443 | 489 | 293 | 218 | 0.814 | 314 | 265 | 195 |

Example 4

Example 4 illustrates one embodiment of the synthetic preparation of a polyboronic compound having the following structure. This example can be used to illustrate how polyboronic compounds are generally synthesized. The synthesis scheme can be extended to other type of polyboronic compounds.

In this example, a 150 mL 3-necked round bottom flask was equipped with a temperature indicator, a pressure-equalizing addition funnel and a reflux condenser guarded with a CaCl$_2$ drying tube. Into the flask was added 7.3 g tris(2-aminoethyl)amine, followed with 15 g anhydrous MeOH. Under nitrogen, 20.8 g freshly distilled trimethyl borate was transferred into the addition funnel and was then diluted with 6.9 g anhydrous MeOH. Under magnetic agitation, the trimethyl borate solution was added drop by drop into the flask at a temperature below 40° C. After the completion of the addition, the resultant solution was allowed to stand at room temperature for 30 minutes and then heated to reflux for at least 4 hours. The resulting compound

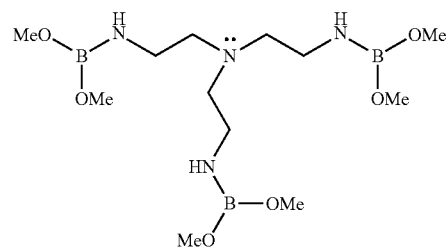 [SMILES: COB(NCCN(CCNB(OC)OC)CCNB(OC)OC)OC]

(and its other ester analogs, such as ethyl boronate, etc.) can be used as a crosslinking agent in accordance with embodiments of the present invention, such as those described in Example 5.

TABLE 3

| | 25 ppt GW-3, 0.4 mmol XLB | | | | 25 ppt GW-3, 3 gpt CXB-10 | | |
|---|---|---|---|---|---|---|---|
| | | Viscosity (cP) at | | | | Viscosity (cP) at | |
| Time, min | n' | 40 sec$^{-1}$ | 100 sec$^{-1}$ | 170 sec$^{-1}$ | n' | 40 sec$^{-1}$ | 100 sec$^{-1}$ | 170 sec$^{-1}$ |
| 2.1 | 0.4827 | 1091 | 568 | 389 | 0.3783 | 3924 | 2220 | 1596 |
| 32.1 | 0.3170 | 1648 | 923 | 660 | 0.2807 | 1354 | 700 | 478 |
| 62.1 | 0.4061 | 1646 | 1047 | 806 | 0.3011 | 1332 | 702 | 485 |
| 92.1 | 0.3914 | 1433 | 918 | 709 | 0.3098 | 1453 | 772 | 535 |
| 122.1 | 0.4074 | 1335 | 824 | 623 | 0.4278 | 1355 | 802 | 592 |
| 152.1 | 0.5785 | 1264 | 883 | 717 | 0.3857 | 1166 | 664 | 479 |
| 182.1 | 0.6394 | 1169 | 872 | 736 | 0.1443 | 1337 | 610 | 388 |

Example 5

In Example 5, the viscoelastic properties (n') and viscosities (cP) of two crosslinked guar polymer systems were compared. 25 ppt of GW-3 was crosslinked with 0.4 mmol compound prepared in Example 4 and 4 gpt 25% sodium hydroxide (NaOH) at 150° F. and compared with an optimized crosslinked system that was prepared by crosslinking 25 ppt of GW-3 with CXB-10, which is commercially available from Baker Hughes Incorporated. As shown in Table 3, the results clearly demonstrate that these polyboronic compounds used in embodiments of the present invention can effectively lower polymer loading for fracturing stimulation.

Example 6

In this example, the vortex closure time for linear gel guar was determined for non-delayed crosslinker (PAB) and delayed crosslinker (DPAB) prepared in accordance with the following reaction schematic pathway:

Reaction Scheme 1

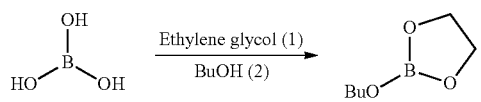

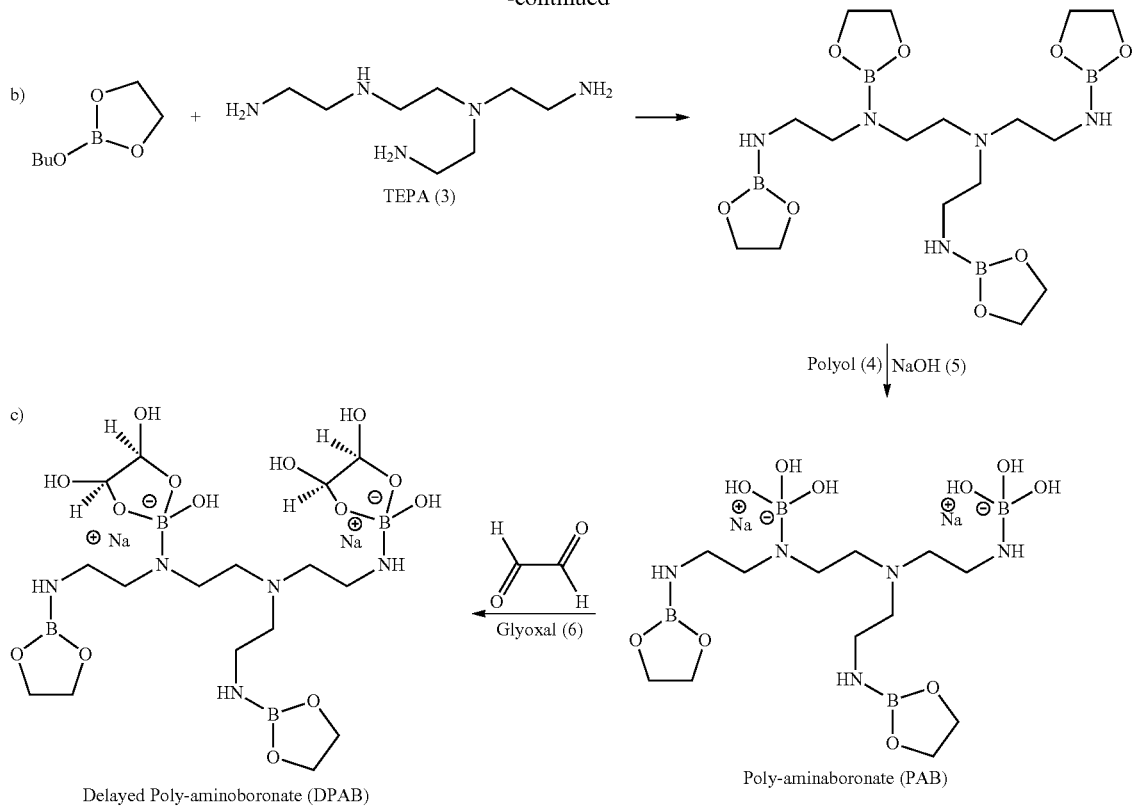

Delayed Poly-aminoboronate (DPAB)

Poly-aminaboronate (PAB)

The molecular size of PAB or DPAB means crosslink with guar or its derivatives can occur well below the critical overlap concentration (C*), thus lower loading of polymer can be utilized for crosslinking compared to conventional fluids.

In this Example, about 60 to 85 g of ethylene glycol and 40 g of n-butanol were added into a 500 mL three neck round bottom flask equipped with a thermometer, and a Dean Stark adaptor equipped with a reflux condenser. About 25 g (0.40 mol) of boric acid was added to the flask and heated under reflux with magnetic agitation until approximately 21 g (1.16 moles) of water was collected. The reaction mixture was cooled down to room temperature and 15.2 g (0.080 moles) of tetraethylenepentamine (TEPA) slowly added. The reaction mixture was then heated at 150° C. until a viscous yellow liquid was formed. The reaction mixture was cooled to room temperature accompanied by steps 4-5 for PAB or steps 4-6 for DPAB. A polyol was added to the crosslinker mixture during synthesis to improve the stability and shelf life of the crosslinker.

1) Non-delayed crosslinker (PAB) synthesis. 8.20 g of polyol (sorbitol, pentaerythritol, dipentaerythritol, or N-methylglucamine) were added to the reaction mixture, heated for 1 hour, cooled, and treated with 50% caustic as shown in steps 4 and 5 of reaction scheme 1. A yellow liquid was obtained as the final solution.

(2) Delayed crosslinker (DPAB) synthesis. 8.20 g (0.45 moles) of sorbitol was added to the reaction mixture, heated for 1 hour, cooled and treated with 50% caustic, accompanied by addition of 60.0 mL of glyoxal (40%) solution at room temperature. An amber colored liquid was obtained as the final solution.

Vortex closure experiments were carried out according to API-R39. 250 g of hydrated guar gum was weighed into a Waring blender jar equipped with three bladed paddle stirrers. Agitation was carried out at 1500 rpm, until a vortex of fluid was observed. A buffer solution was added to the solution, accompanied by the crosslinker. The time from injection of crosslinker into the Waring jar up to when the vortex closes is the vortex closure time. The vortex closure time is usually dependent on the buffer, crosslinker and polymer loading. Systematic investigations of crosslinker delay properties of the poly-aminoboronates (PAB) crosslinkers as a function of polyols, such as sorbitol, pentaerythritol, dipentaerythritol, or N-methylglucamine, were carried out. Preliminary results of the investigation showed vortex closure in the range of 22-34 s for a 25 ppt (pound per thousand gallon) of guar linear gel in fresh water (buffer and crosslinker loading of 1.20 gpt NaOH (25%), and 2.8-3.4 gpt (gallon per thousand gallon), respectively). A summary of vortex closure time for guar linear gel containing optimized buffer, and delayed crosslinker loadings at room temperature is set forth in Table 4 below.

TABLE 4

| Crosslinker | Guar loading (ppt) | Buffer loading (gpt) | Crosslinker loading (gpt) | Vortex closure (s) |
|---|---|---|---|---|
| DPAB | 25 | 1.2 caustic (25%) | 3.0 | 93 |
| DPAB | 25 | 2.4 caustic (25%) | 4.0 | 150 |
| DPAB (additional 4% glyoxal) | 25 | 2.4 caustic (25%) | 4.2 | 176 |
| DPAB (additional 8% glyoxal) | 25 | 2.6 caustic (25%) | 4.6 | 207 |

TABLE 4-continued

| Crosslinker | Guar loading (ppt) | Buffer loading (gpt) | Crosslinker loading (gpt) | Vortex closure (s) |
|---|---|---|---|---|
| DPAB (additional 15% glyoxal) | 25 | 3.0 caustic (25%) | 4.6 | 240 |

Figure 3:
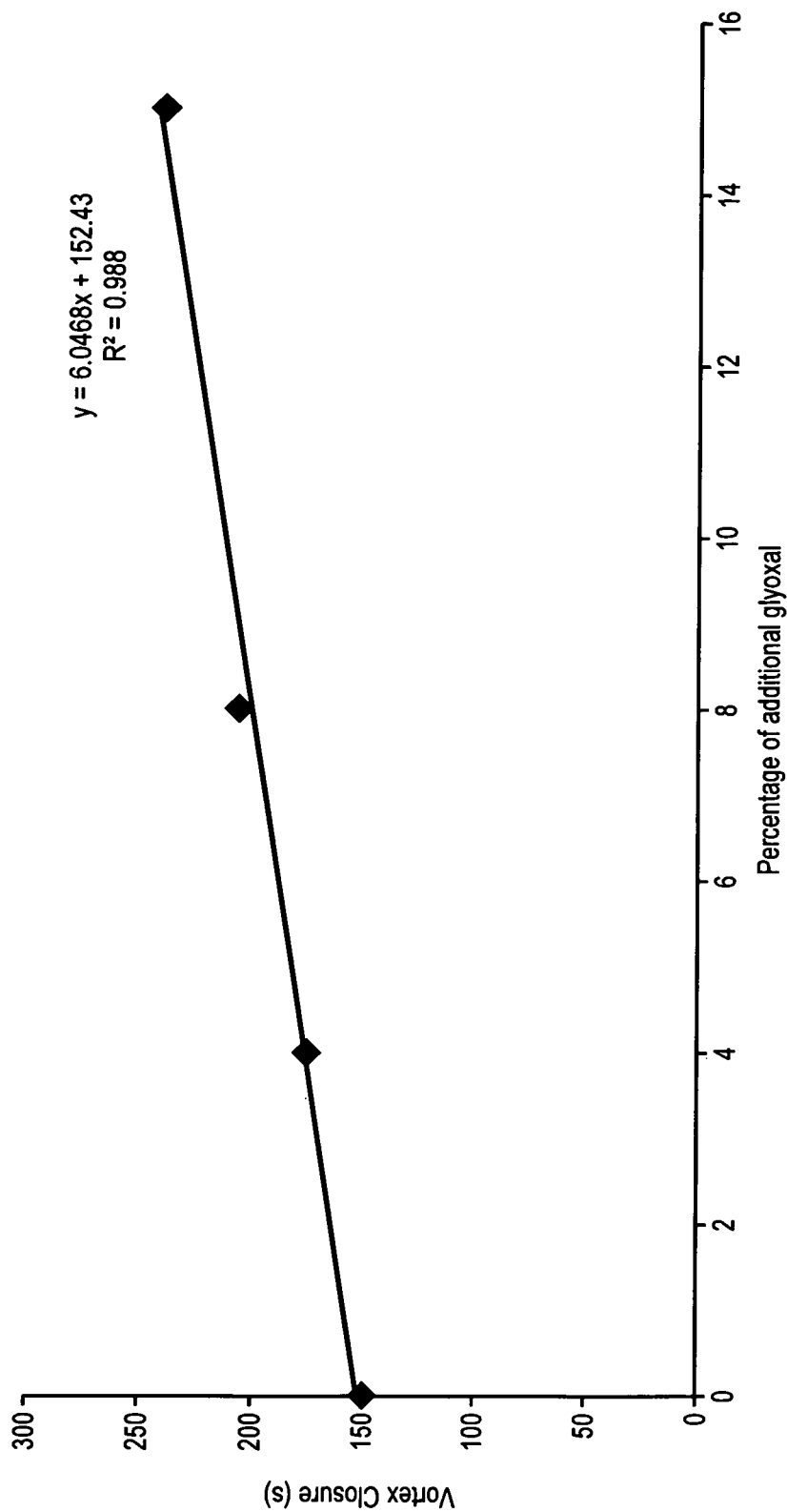
FIG. 3 illustrates the linear dependence between the vortex closure time and glyoxal in the production of a delayed polyboronic crosslinking agent in accordance with embodiments of the present invention.

The vortex closure of the delayed crosslinker in 25 ppt guar linear gel in fresh water, at a buffer, crosslinker loading of 2.4-3.0 gpt, and 4.0-4.6 gpt, respectively was in the range of 150-240 s. Table 1 also illustrates the lengthening of vortex closure time by the addition of extra amounts of glyoxal to delayed boron crosslinkers. For instance, varying additional glyoxal from 0, 4, 8 and 15%, led to a steady increase in vortex closure time (delay) from 150 s to 176 s, 207 s and 240 s, respectively. It is likely that reaction between excess glyoxal and hydroxides (caustic) of poly-aminoboronate (PAB) effectively blocks the borates sites of the crosslinker, resulting in improved vortex closure. A plot of vortex closure time versus percentage of additional glyoxal for the polyboronic crosslinkers is illustrated in FIG. 3. Table 4 also illustrates that the polyboronic crosslinkers exhibit adjustable delay characteristics by changing the loading of the dialdehyde.

The polyboronic compounds were evaluated as crosslinkers in guar fluids on a Fann 50 rheometer, API RP-39, by placing 48 g of gel in the Fann 50 cup (RIB5 cup and bob geometry) and positioning the cup on the Fann viscometer. The sample was pressurized to about 300 psi with $N_2$, pre-conditioned by shearing at 100 $s^{-1}$ for 1 minute. Afterwards, a rate sweep of 100 $s^{-1}$, 80 $s^{-1}$, 60 $s^{-1}$ and 40 $s^{-1}$ was made and repeated every 30 minute. The initial rate sweep was performed at room temperature, and the fluid heated up to the experimental temperature. The interim rate between sweeps was 100 $s^{-1}$. The shear rates, as well as corresponding stresses were used to determine the power law indices, n' and K.

Figure 4:
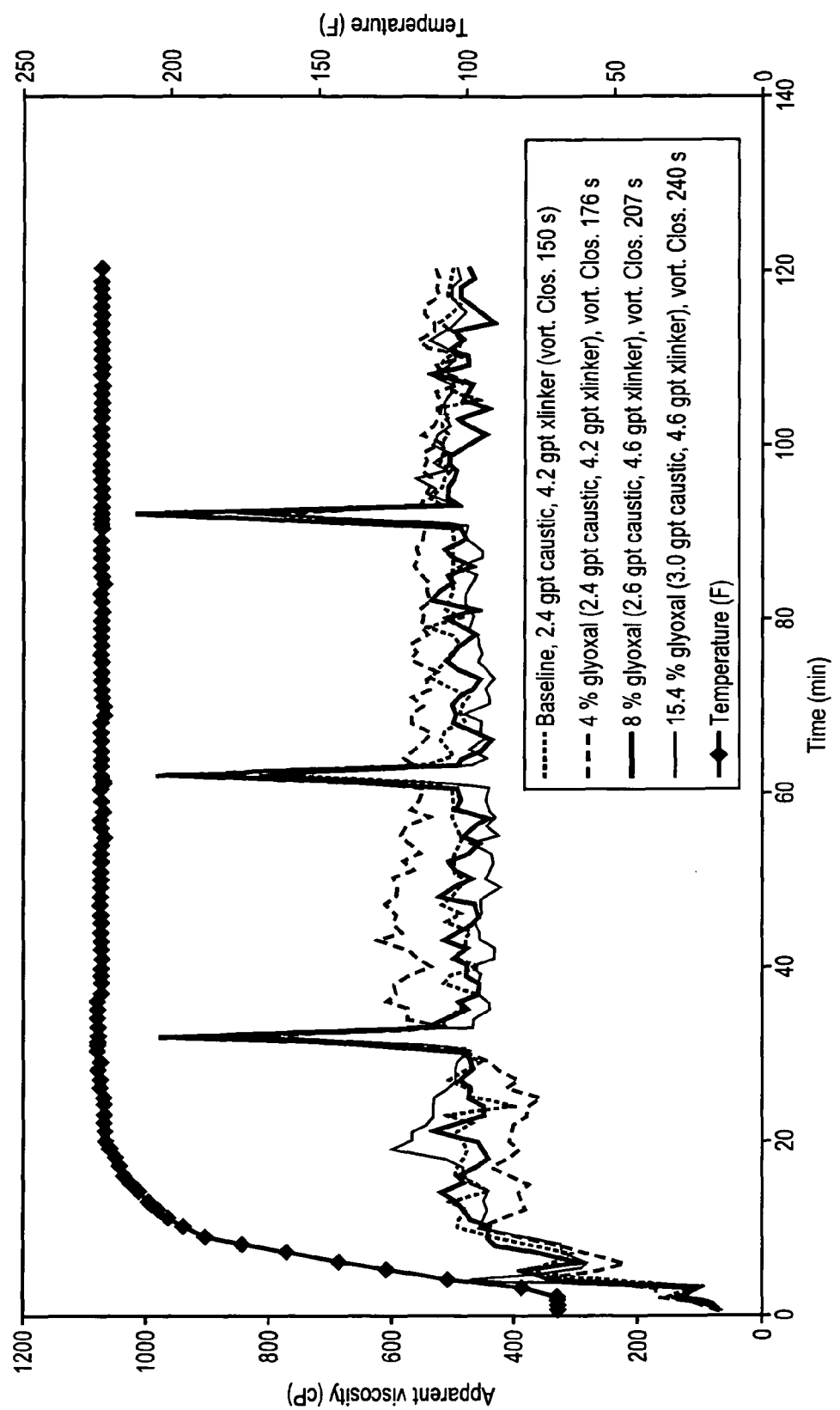
FIG. 4 depicts the rheology profile of three batches of borates crosslinkers with additional glyoxal (4-15%) compared to baseline crosslinked fluid in accordance with embodiments of the present invention.

A baseline fluid containing 25 ppt guar linear gel in fresh water, 0.50 biocide, 1 gpt clay control agent, 1 gpt flow-back surfactant, 2.4-3.0 gpt NaOH (25%) and 4.0-4.6 gpt of DPAB was prepared. Glyoxal in the amount of 4%, 8% and 15.4% was added to three separate batches of the baseline fluid. The rheology performance of the three separate batches containing glyoxal was seen to be uncompromised relative to the baseline delayed fluid at testing temperature of 225° F. The rheology profile of the baseline and three batches of fluid containing glyoxal are illustrated in FIG. 4. The typical rheology behavior of delayed fracturing fluid involves the slow viscosity build-up with increasing temperature until maximum viscosity is achieved. The same trend is seen with the new delayed crosslinker (DPAB).

Figure 5:
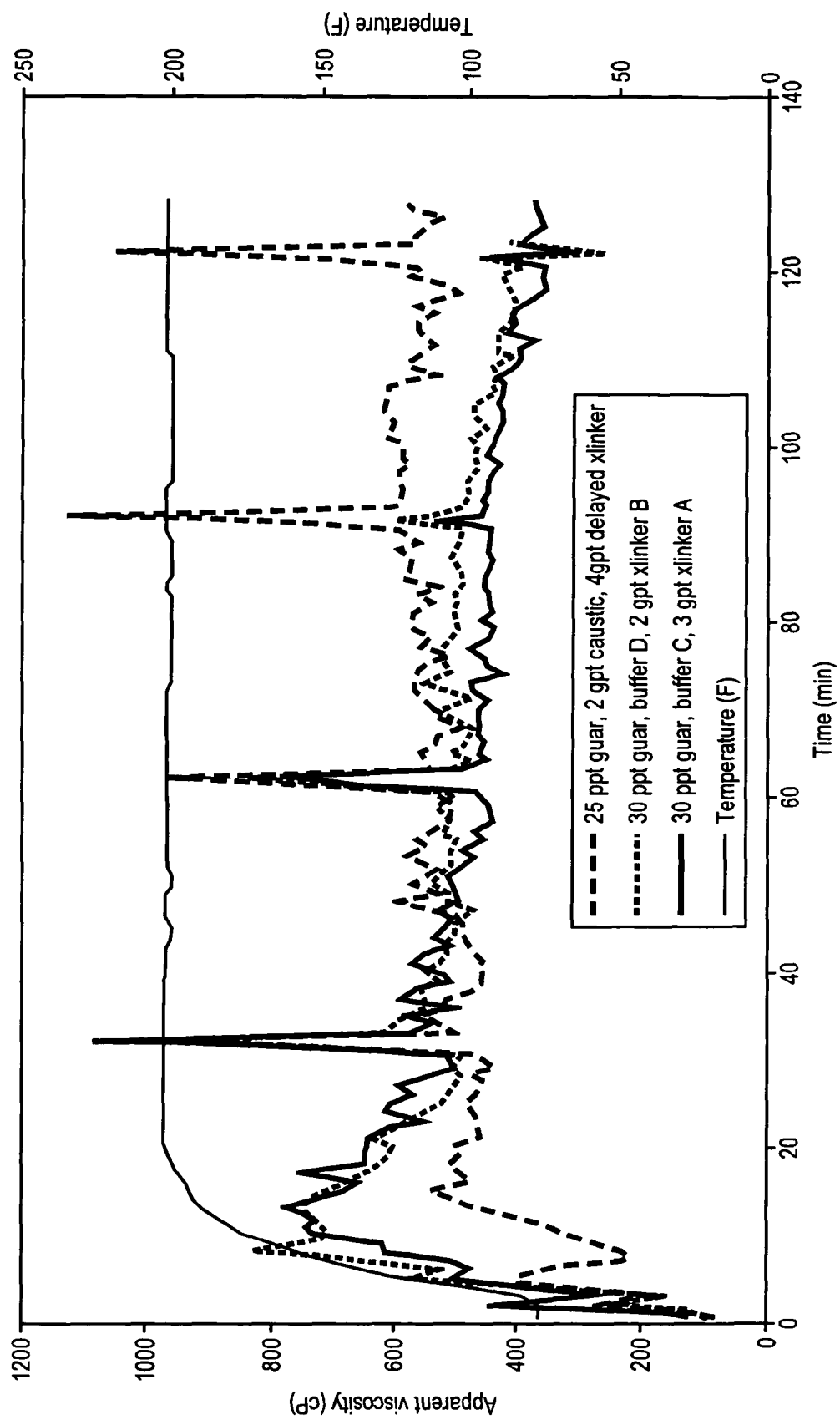
FIG. 5 depicts the rheology profile of fluids having different loadings of guar in fluids crosslinked with a delayed crosslinker in accordance with the embodiments of the present invention.

A fluid was prepared containing 0.50 gpt biocide, 1 gpt clay control agent, 1 gpt flow-back surfactant, and 1 gpt gel stabilizer, guar and crosslinker. One fluid contained 35 ppt guar crosslinked with 3 gpt XLW-56 borate w/glyoxal, (conventional "xlinker A") and a second fluid contained 30 ppt guar crosslinked with 4 gpt of delayed crosslinked (DPAB) fluid. The rheology of baseline with shear sweeps at 100, 80, 60 and 40 $s^{-1}$ was determined at a temperature range of 200° F. to 250° F. The result at 200° F. is illustrated in FIG. 5, and show the rheology performance of the DPAB crosslinker with 20% less polymer (guar) to be comparable to or better than baseline crosslinked fluids containing the conventional crosslinker. A similar trend was observed at testing temperature of 225 and 250° F. Thus a polymer saving of 20% could be achieved with using our new delayed crosslinker compared to crosslinker A. Less polymer usage by the delayed crosslinker relative to conventional fracturing fluid translates to less damage to the subterranean formation and increased productivity.

The flow behavior index (n') value less than 1 (n'<1) for crosslinked fluids as described by the Power Law theory, is indicative of a shear thinning or fluid exhibiting non-Newtonian properties. The power law parameters (flow behavior index) obtained from all rheology experiments for DPAB and PAB crosslinked fluid as shown in FIG. 5 were less than 0.60 after two hours, indicative of a shear thinning fluid or high performing fluid. The viscosity after two hours for a 25 ppt guar in fresh water crosslinked with DPAB or PAB crosslinked fluid exceeded 500 cP without compromise in performance at 225° F.

Example 6

Fluid loss experiments were conducted, in accordance with ISO 13503, on a 25 ppt guar boron crosslinked fluid at 200° F. and 225° F. Three especially hardened OFI Filter Press papers with diameter of 2.5 inches were used for the experiment at 200° F., and the wall building coefficient ($C_{III}$) was 0.002 ft/min$^{1/2}$. The results indicated the formation of a good filter cake by fluid crosslinked with DPAB, minimizing potential fluid loss to the formation. Fluid loss tests were also carried with an OFITE ceramic filter disc (diameter 2.5 inch and 0.25 inch thick) with mean pore throat of 3 μM in air and permeability of 750 mD in air. No filtrate through the ceramic filter disc was observed at 225° F. possible due to formation of a thick layer of filter cake on the filter surface, thereby blocking the pores.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the methods described herein without departing from the concept, spirit and scope of the invention. More specifically, it will be apparent that certain agents that are chemically related can be substituted for the agents described herein while the same or similar results would be achieved. All such similar substitutes and modifications apparent to those skilled in the art are deemed to be within the scope and concept of the invention.

What is claimed is:

1. A method of fracturing a subterranean formation comprising the steps of:
   a. blending together water and a hydratable polymer capable of gelling in the presence of a crosslinking agent;
   b. allowing the hydratable polymer to hydrate to form a hydrated polymer solution; and
   c. adding a crosslinking agent comprising a polyboronic compound to the hydrated polymer solution to produce a crosslinked fracturing fluid,
   wherein the polyboronic compound is of the formula:

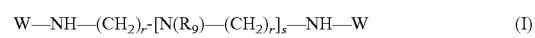

wherein:
   s is 1 to 6;
   each $R_9$ is independently selected from the group consisting of —W or —$(CH_2)_r$—NH—W;
   each r is independently selected from 2 to 6;

W is a substituent of the formula:

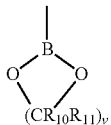

(II)

v is either 2 or 3, provided v cannot be both 2 and 3 in the same compound;

each $R_{10}$ is independently selected from either —H or $R_{12}$ and each $R_{11}$ is independently selected from either —H or —OH, provided that $R_{10}$ and $R_{11}$ in at least one W substituent group is $R_{12}$ and —OH, respectively;

each $R_{12}$ is independently selected from the group consisting of a linear or branched $C_1$-$C_6$ alkyl or alkenyl group, optionally substituted with —X or —$OR_{13}$;

X is —Cl or —Br; and $R_{13}$ is a $C_1$-$C_6$ alkyl group; and d. pumping the fluid into the subterranean formation to fracture the formation.

2. The method of claim 1, wherein at least two of the W substituent groups of the polyboronic compound are of the formula (II).

3. The method of claim 1, wherein s is 2 or more.

4. The method of claim 3, wherein the number of W substituent groups being of formula (II) is from 1 to 4.

5. The method of claim 1, wherein $R_9$ is —$(CH_2)_r$—NH—W, each r is 2, s is and v is 2.

6. The method of claim 1, wherein the polyboronic compound is of the formula:

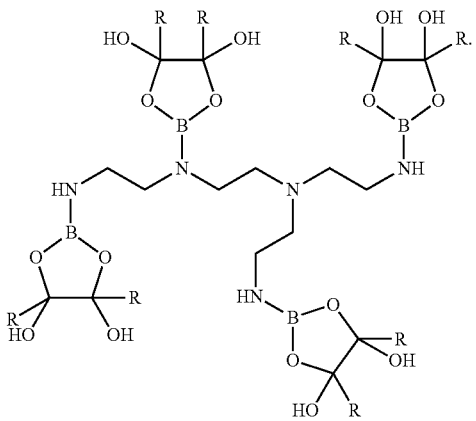

(III)

7. The method of claim 1, wherein the polyboronic compound is prepared by:

(i) forming a polyaminoboronate by contacting a cyclic borate ester with a polymeric amine of the formula $H_2N$—$(CH_2)_r$-[NH—$(CH_2)_r]_s$—NH, wherein r is 2 to 6 and s is 1 to 6 and further wherein the cyclic borate ester is of the formula:

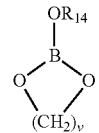

(IV)

wherein $R_{14}$ is the alkyl chain of a alcohol having a boiling point greater than water residue; and (ii) reacting the polyaminoboronate with a di-aldehyde or di-ketone in caustic to produce the polyboronic compound.

8. The method of claim 7, wherein the polymeric amine comprises ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, or combinations thereof.

9. The method of claim 1, wherein the polyboronic compound is prepared by:

(a) contacting a polymeric amine with a cyclic borate ester to form a polyaminoboronate, wherein the cyclic borate ester is of the formula:

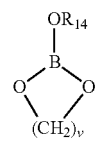

(IV)

wherein $R_{14}$ is the alkyl chain of an alcohol having a boiling point greater than water residue; and wherein the polymeric amine comprises ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, or combinations thereof, and (b) reacting the polyaminoboronate with a di-aldehyde or diketone in the presence of caustic to render the polyboronic compound of formula (I).

10. The method of claim 9, wherein the cyclic borate ester is prepared by reacting boric acid and a diol in the presence of an alcohol, ROH, having a boiling point higher than the boiling point of water.

11. A method of fracturing a subterranean formation comprising the steps of:

a. crosslinking a fracturing fluid comprising a hydratable polymer by contacting the fracturing fluid with a polyboronic compound to produce a crosslinked fracturing fluid, wherein the polyboronic compound is of the formula:

W—NH—$(CH_2)_r$-[N($R_9$)—$(CH_2)_r]_s$—NH—W     (I)

wherein:

s is 1 to 6;

each $R_9$ is independently selected from the group consisting of —W or —$(CH_2)_r$—NH—W;

each r is independently selected from 2 to 6;
W is a substituent of the formula:

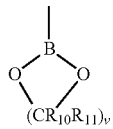
(II)

v is either 2 or 3, provided v cannot be both 2 and 3 in the same compound;
each $R_{10}$ is independently selected from either —H or $R_{12}$ and each $R_{11}$ is independently selected from either —H or —OH, provided that $R_{10}$ and $R_{11}$ in at least one W substituent group is $R_{12}$ and —OH, respectively;
each $R_{12}$ is independently selected from the group consisting of a linear or branched $C_1$-$C_6$ alkyl or alkenyl group, optionally substituted with —X or —$OR_{13}$;
X is —Cl or —Br; and
$R_{13}$ is a $C_1$-$C_6$ alkyl group; and
b. injecting the crosslinked fracturing fluid into the subterranean formation to fracture the formation.

12. The method of claim 11, wherein at least two of the W substituent groups are of the formula (II).

13. The method of claim 11, wherein s is 2 or more.

14. The method of claim 13, wherein the number of W substituent groups being of formula (II) is from 1 to 4.

15. The method of claim 11, wherein $R_9$ is —$(CH_2)_r$—NH—W, each r is 2, s is and v is 2.

16. The method of claim 15, wherein the polyboronic compound is of the formula:

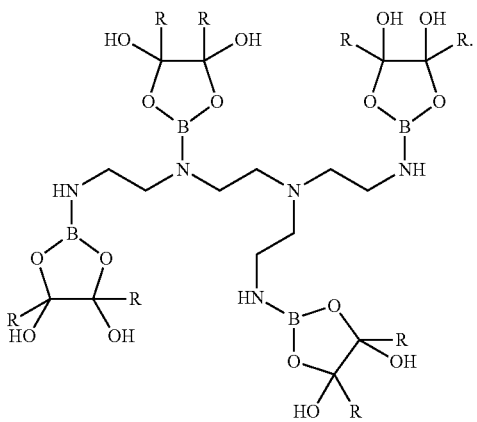
(III)

17. The method of claim 1, wherein the hydratable polymer is selected from the group consisting of guar gum, a guar gum derivative, locust bean gum, karaya gum, a cellulosic derivative or a mixture.

18. The method of claim 17, wherein the hydratable polymer is guar gum or a guar gum derivative or a mixture thereof.

19. The method of claim 11, wherein the hydratable polymer is guar gum, carboxymethyl guar, hydroxypropyl guar, carboxymethyl hydroxypropyl guar or a mixture thereof.

20. A method of fracturing a subterranean formation comprising pumping into the formation at a pressure sufficient to fracture the formation a fracturing fluid having a critical crosslinking concentration, $C_{cc}$, less than about 15.5 ppt and prepared from:
(i) a hydratable polymer selected from guar gum, derivatized guar or a mixture thereof; and
(ii) a polyboronic compound of the formula:

$$W—NH—(CH_2)_r-[N(R_9)—(CH_2)_r]_s—NH—W \quad (I)$$

wherein:
s is 1 to 6;
ach $R_9$ is independently selected from the group consisting of —W or —$(CH_2)_r$—NH—W;
each r is independently selected from 2 to 6;
W is a substituent of the formula:

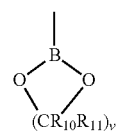
(II)

v is either 2 or 3, provided v cannot be both 2 and 3 in the same compound;
each $R_{10}$ is independently selected from either —H or $R_{12}$ and each $R_{11}$ is independently selected from either —H or —OH, provided that $R_{10}$ and $R_{11}$ in at least one W substituent group is $R_{12}$ and —OH, respectively;
each $R_{12}$ is independently selected from the group consisting of a linear or branched $C_1$-$C_6$ alkyl or alkenyl group, optionally substituted with —X or —$OR_{13}$;
X is —Cl or —Br; and
$R_{13}$ is a $C_1$-$C_6$ alkyl group; and
b. injecting the fluid into the subterranean formation to fracture the formation.

21. The method of claim 20, wherein the hydratable polymer is guar gum, derivatized guar or a mixture thereof.

22. The method of claim 20, wherein at least two of the W substituent groups of the polyboronic compound are of the formula (II).

23. The method of claim 20, wherein the number of W substituent groups being of formula (II) is from 1 to 4.

24. The method of claim 20, wherein $R_9$ is —$(CH_2)_r$—NH—W, each r is 2, s is and v is 2.

25. The method of claim 20, wherein the polyboronic compound is of the formula:

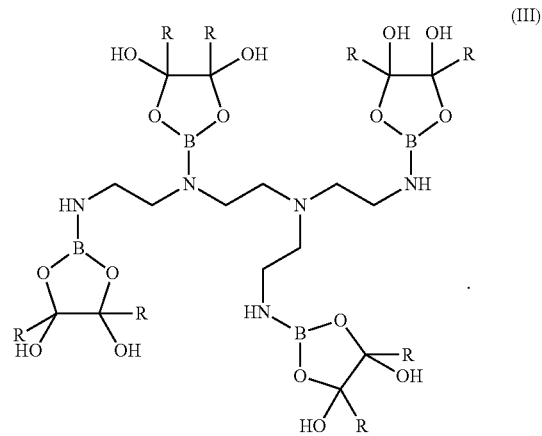
(III)

* * * * *